United States Patent [19]
Johnston et al.

[11] Patent Number: 5,874,574
[45] Date of Patent: Feb. 23, 1999

[54] PROCESS OF CRYSTALLIZING 2,4,6,8,10,12-HEXANITRO-2,4,6,8,10,12,-HEXAAZATETRACYCLO [5.5.0.0.5,9.03,11]-DODECANE

[75] Inventors: Harold Eugene Johnston, Dickson, Tenn.; Robert B. Wardle, Logan, Utah

[73] Assignee: Cordant Technologies Inc., Salt Lake City, Utah

[21] Appl. No.: 991,432

[22] Filed: Dec. 16, 1997

Related U.S. Application Data

[60] Provisional application No. 60/033,392 Dec. 17, 1996.
[51] Int. Cl.$^6$ .................................................. C07D 257/02
[52] U.S. Cl. ................................................................ 540/475
[58] Field of Search ............................................. 540/475

[56] References Cited

U.S. PATENT DOCUMENTS

| | | | |
|---|---|---|---|
| 4,638,065 | 1/1987 | Svensson et al. | 544/196 |
| 4,785,094 | 11/1988 | Levinthal | 540/475 |
| 4,794,180 | 12/1988 | Heinemeyer et al. | 540/475 |
| 5,124,493 | 6/1992 | Lukasavage et al. | 540/475 |
| 5,132,409 | 7/1992 | Felder et al. | 534/10 |
| 5,268,469 | 12/1993 | Lukasavage et al. | 540/475 |
| 5,623,168 | 4/1997 | Fels et al. | 264/3.6 |
| 5,682,004 | 10/1997 | Fels et al. | 86/21 |
| 5,693,794 | 12/1997 | Nielsen | 540/554 |
| 5,707,634 | 1/1998 | Schmitt | 424/400 |
| 5,723,604 | 3/1998 | Cannizzo et al. | 540/556 |

FOREIGN PATENT DOCUMENTS

| | | |
|---|---|---|
| 0 246 526 A1 | 5/1987 | European Pat. Off. |
| WO 90/03782 | 4/1990 | WIPO. |
| WO 93/06065 | 4/1993 | WIPO. |
| WO 97/00873 | 1/1997 | WIPO. |
| WO 97/20785 | 6/1997 | WIPO. |

OTHER PUBLICATIONS

"Crystallization", Encyclopedia of Chemical Technology, vol. 7, 1993, pp. 720–721.
Bachmann et al., James Chem Soc., May 1949, vol. 71, pp. 1842–1845.

*Primary Examiner*—Mukund J. Shah
*Assistant Examiner*—Pavanaram K. Sripada
*Attorney, Agent, or Firm*—Pillsbury Madison & Sutro LLP

[57] ABSTRACT

A process of crystallizing CL-20 is disclosed. In the process, a wet CL-20 solvent/CL-20 solution is dried by azeotropic distillation of a CL-20 solvent/water azeotrope. Removal of water from the CL-20 solution permits crystallization of high density CL-20. A low density, CL-20 non-solvent is added to the resulting dry CL-20 solvent/CL-20 solution to cause precipitation of ε-polymorph CL-20. The CL-20 crystals are separated from the non-solvent and the solvent by adding sufficient water to displace the non-solvent and the solvent from the surface of the CL-20 crystals. In this fashion, the ε-polymorph CL-20 is made wet for later handling, packaging, and shipping.

27 Claims, 2 Drawing Sheets

PROCESS OF CRYSTALLIZING 2,4,6,8,10,12-HEXANITRO-2,4,6,8,10,12,-HEXAAZATETRACYCLO [5.5.0.0.5,9 0 3,11]-DODECANE

RELATED APPLICATIONS

This is a U.S. complete application claiming the filing date benefit of U.S. Provisional application 60/033,392 filed Dec. 17, 1996.

FIELD OF THE INVENTION

The present invention relates to an improved method of crystallizing 2,4,6,8,10,12-hexanitro-2,4,6,8,10,12-hexaazatetracyclo[$5.5.0.0^{5,9}0^{3,11}$]-dodecane, hereinafter referred to as "CL-20."

BACKGROUND OF INVENTION

The current process for crystallizing CL-20 uses chloroform to precipitate CL-20 from ethyl acetate. Chloroform and ethyl acetate cannot be effectively separated by distillation for reuse which results in the continual discharge of a chlorinated waste stream. It is harmful to the environment and economically wasteful to continually discharge a chlorinated organic solvent such as chloroform. As a chlorinated solvent, chloroform may potentially contribute to ozone depletion. Thus, it would be an advancement in the art to provide a process for crystallizing CL-20 which does not require or discharge chlorinated solvents and which permits efficient recycling of the solvent within the crystallization process.

A great number of skilled workers in the art have attempted to use non-chlorinated solvents in crystallizing CL-20. But only chloroform has consistently and reproducibly produced the desirable $\epsilon$-polymorph of CL-20.

In addition, other current CL-20 crystallization techniques do not consistently produce high quality CL-20. CL-20 is known to have several different crystal polymorphs, one of which is a high density phase referred to herein as the $\epsilon$-polymorph. CL-20 produced according to prior art techniques is predominantly a low density crystal polymorph, referred to herein as the $\alpha$-polymorph. $\epsilon$-polymorph CL-20 possess superior ballistic properties compared to the commonly formed $\alpha$-polymorph. The crystallization conditions which produce $\epsilon$-polymorph CL-20 are not well understood in the art; therefore, it would be an advancement in the art to provide a process of crystallizing CL-20 which produces predominantly $\epsilon$-polymorph CL-20.

Such processes for crystallizing CL-20 are disclosed and claimed herein.

SUMMARY OF THE INVENTION

The present invention is directed to a process of crystallizing CL-20. In the process, a quantity of CL-20 is dissolved in a solution containing a CL-20 solvent, such as ethyl acetate, and water. The resulting mixture consists of two liquid phases: an aqueous phase and a wet solvent phase. The pH of the aqueous phase can be tested and adjusted at this point as desired. The CL-20 is dissolved in the wet solvent phase. The wet CL-20 solvent phase is then dried by removing a solvent/water azeotrope according to conventional distillation techniques, thereby forming a dry solvent phase containing the CL-20. It has been found that crystallization of dry CL-20 results in the formation of predominantly $\epsilon$-polymorph CL-20.

A low density nonpolar CL-20 non-solvent, such as hexane, cyclohexane, heptane, octane (including 2,2,2-trimethylpentane), benzene, toluene, xylene, mineral oil, petroleum ethers, and ligroin, is added to the dry CL-20 solvent phase to cause crystallization of $\epsilon$-polymorph CL-20. The low density nonpolar non-solvent preferably has a density less than water. The CL-20 crystals are then separated from the non-solvent and the solvent by adding sufficient water to displace the non-solvent and the solvent from the surface of the $\epsilon$-CL-20 crystals. In this fashion, the $\epsilon$-polymorph CL-20 is made wet for later handling, packaging, and shipping. The ratio of water to CL-20 should typically range from 1:7 to 3:1, by volume. Of course, more water can easily be used in the system, but larger quantities of water will require larger equipment for separating and recycling the water.

The wet CL-20 is collected and the CL-20 non-solvent, CL-20 solvent, and excess water are removed to separate and recycle the individual solvents.

DETAILED DESCRIPTION OF THE INVENTION

Figure 1:
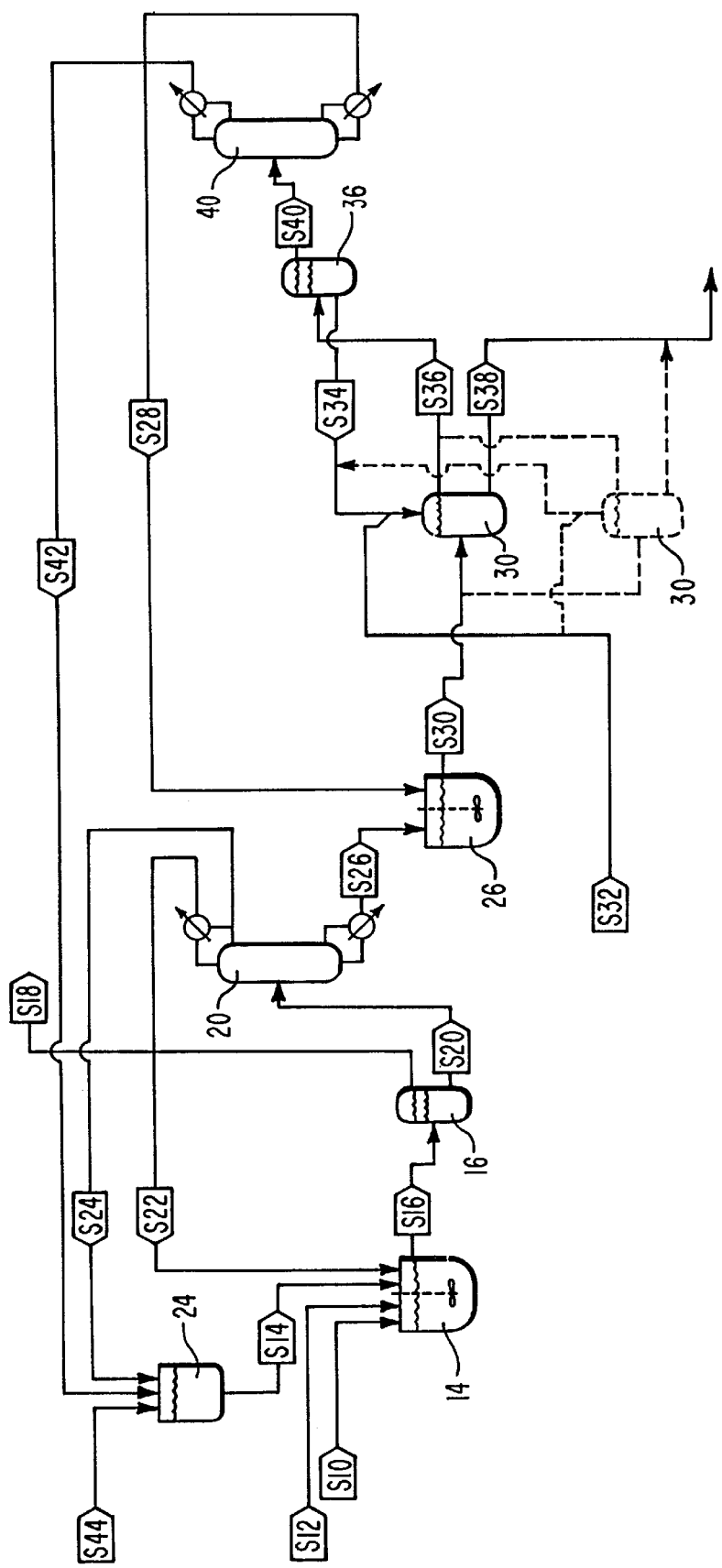
FIG. 1 is a schematic representation of a system for crystallizing CL-20 according to the present invention.

The present invention is directed to a process of crystallizing CL-20. One currently preferred process and system for crystallizing CL-20 is illustrated schematically in FIG. 1. An overall CL-20 crystallization system within the scope of the present invention, designated generally at 10. In the process, a crude CL-20 stream S10, a water stream S12, and an ethyl acetate stream S14 are combined in dissolver 14 wherein the CL-20 is dissolved in excess ethyl acetate (a CL-20 solvent).

With the CL-20 dissolved in a solvent, a base (in either solid or solution form) may be added to ensure removal of all acidic species. The pH of the aqueous layer can be tested and adjusted to a pH greater than 7 with $Na_2CO_3$ or a similar base ($NaHCO_3$, $K_2CO_3$, $KHCO_3$, NaOH, KOH, etc.). It has been found that the presence of acidic species in crystallized CL-20 increases the sensitivity to impact and friction. The base can be added to the system at any point where the CL-20 is dissolved in the solvent. In some cases it is desirable to wait and add base as a final step prior to CL-20 crystallization.

Although the crystallization system is described herein using ethyl acetate as the CL-20 solvent, one skilled in the art will appreciate that other solvents can also be used, such as low molecular weight polar solvents, including esters, ketones, and cyclic ethers, and more specifically, methyl acetate, isopropyl acetate, butyl acetate, THF, and MEK. As used herein, the term "CL-20 solvent" or "solvent" includes solvents that have high CL-20 solubility (>20% weight/volume (g/ml)), form a water azeotrope, have a low boiling temperature (<90° C.) to permit easy distillation, have relatively low volatility so that in-process loss is insignificant, and do not form an azeotrope with the CL-20 non-solvent described below. Ethyl acetate is a currently preferred solvent.

Two immiscible liquid phases flow from the dissolver 14 to a first decanter 16 in a first decanter inlet stream S16. The two liquid phases separate in the first decanter 16. The upper water rich liquid phase flows out of the process in waste water stream S18, which is the only waste stream in the crystallization system 10. The lower liquid phase, which contains the dissolved CL-20, flows on to a solution dryer 20 in stream S20.

The solution dryer distills the ethyl acetate/water azeotrope from the CL-20 solution leaving the CL-20 solution nearly free of water. It has been found that the CL-20 should be essentially anhydrous (less than about 1.5%, by weight, water) in order to crystallize into a desirable, high density crystal polymorph ($\epsilon$-polymorph). If too much water is present, then a lower density crystal polymorph ($\alpha$-polymorph), or a mixture of polymorphs, is formed. Thus, removal of water in the solution dryer is very important to obtain high density CL-20. Other drying techniques not illustrated in FIG. 1 can also be used to dry the CL-20 solution such as the use of a desiccant.

It preferable to operate the solution dryer 20 under conditions which remove the ethyl acetate/water azeotrope without reducing the ethyl acetate needed to keep the CL-20 soluble. Removal of too much ethyl acetate may cause CL-20 to crystallize in the solution drier column. The solution drier is preferably operated at low temperature under vacuum pressure. Those skilled in the art will appreciate that a wide range of operating temperatures, reflux ratios, column heights, and pressures are possible to achieve the desired separation.

In one currently preferred solution dryer embodiment, the top stage has a temperature of about 110° F., and the bottom stage has a temperature of about 126° F. The operating pressure is about 5.0 psia at the top and 5.3 psia at the bottom. The solution dryer column is approximately 20 feet tall with 15 trays. The input stream S20 enters the column above tray 2 (with the trays numbered from top to bottom). The molar reflux ratio is about 4.4. Of course, as mentioned above, a wide range of operating conditions are usable by those skilled in the art to obtain the desired separation.

The condensate from the solution dryer 20 separates into two phases: the water rich phase is fed back to the dissolver 14 through stream S22 and the ethyl acetate phase is fed back to the ethyl acetate tank 24 through stream S24. The dry CL-20 solution from the solution dryer 20 flows through crystallizer input stream S26 to crystallizer 26.

In crystallizer 26, the CL-20 is precipitated from the ethyl acetate by the addition of a CL-20 non-solvent. Non-solvents include simple aromatics, such as benzene and the like, and relatively lower carbon number hydrocarbons, such as pentane to dodecanes. In the illustrated embodiment, the CL-20 non-solvent is toluene. Toluene is fed to the crystallizer 26 through toluene stream S28. Other CL-20 non-solvents, such as pentane, hexane, cyclohexane, heptane, octane (including 2,2,2-trimethylpentane), benzene, xylene, mineral oil, petroleum ethers, and ligroin, can also be used to cause crystallization of CL-20. As used herein, the term "CL-20 non-solvent" or "non-solvent" includes nonpolar solvents that have very poor CL-20 solubility (<<1% weight/volume (g/ml)), have significantly different boiling points than the solvent, have a low enough boiling point to be distilled with comparative ease, are not so volatile that in-process loss is significant, do not form an azeotrope with the CL-20 solvent, and are less dense than water so that water can be used to displace the non-solvent. In choosing a CL-20 solvent and non-solvent, the combination must be chosen to maintain the boiling point differential. By preference, the boiling point differential is about 20° C.

In the illustrated embodiment, the CL-20 slurry flows from the crystallizer 26 to a CL-20 recovery tank 30 in CL-20 recovery input stream S30. The CL-20 recovery tank 30 permits safe separation of CL-20 from the flammable crystallizer solvents. This is accomplished by adding water, or another chemically compatible dense, polar solvent, to the CL-20 recovery tank 30. Water is the illustrated dense, polar solvent. Thus, water is added to the CL-20 recovery tank through water streams S32 and S34. Minimal water is preferably used to displace the organic solvents from the CL-20 crystals. At a maximum, the ratio of water to CL-20 should be 3:1, by volume. More preferably, the ratio of water to CL-20 is roughly 1:1, by volume. At a minimum, the ratio of water to CL-20 is 1:7. The minimal amount is required for safe storage and transportation. The maximum should not be exceeded because of extra effort required to remove excess water. The water will also be contaminated with trace solutions of CL-20 and will require treatment prior to discharge.

The crystallization solvents (ethyl acetate/toluene) and water flow through second decanter inlet stream S36 to a second decanter 36 which separates the polar water phase from the nonpolar crystallization liquors. The final CL-20 product, in a water-wet state, leaves the crystallization system 10 in CL-20 outlet stream S38.

The CL-20 crystallization system 10 preferably includes two CL-20 recovery vessels arranged in parallel for alternating use. In FIG. 1, the second CL-20 recovery tank is shown in phantom lines. By having parallel CL-20 recovery tanks, water-wet CL-20 can be recovered from one of the tanks while CL-20 is accumulating in the other tank.

The water phase flows from the second decanter 36 back to the CL-20 recovery tank through water stream S34. The crystallization liquors flow to a solvent separator 40 through solvent stream S40. The solvent separator 40 distills ethyl acetate from toluene for reuse back in the process. Solvent separator 40 utilizes conventional design and operation conditions well known to those skilled in the art of liquid/liquid separations. It will be appreciated that the design and operating conditions of a suitable solvent separator will depend on the solvent and non-solvent used in the system.

In one currently preferred solvent separator embodiment, the top stage (stage 1) operates at a temperature of about 167° F., and the bottom stage (stage 15) operates at a temperature of about 231° F. The column is preferably operated at ambient pressure. The solvent separator is approximately 20 feet tall with 15 trays. The feed stream S40 enters the column above tray 12 (with the trays numbered from top to bottom). The molar reflux ratio is about 5. Of course, as mentioned above, a wide range of operating conditions are usable by those skilled in the art to obtain the desired separation.

The toluene is shown flowing from the solvent separator 40 to the crystallizer 26 through stream S28, and the ethyl acetate is shown flowing to the ethyl acetate tank 24 through stream S42.

To maintain a mass balance in the overall crystallization system 10, a small amount of ethyl acetate must be added to the ethyl acetate tank 24 through ethyl acetate input stream S44 to account for the ethyl acetate leaving the system in waste stream S18. Similarly, a small amount of water must be added to the CL-20 recovery tank 30 to account for the water leaving the system in the final CL-20 outlet stream S38.

A summary of the CL-20 crystallization flow rates for each stream is set forth below in Table 1. Those skilled in the art will appreciate that it is possible to modify the process stream flow rates and compositions described below and still obtain very useful results.

TABLE 1

| Stream | Components: lb/hr | | | | Total Flow lb/hr | Total Flow ft³/hr |
| --- | --- | --- | --- | --- | --- | --- |
| | Water | EtAc | CL-20 | Toluene | | |
| S10 | 3.430 | | 8.000 | | 11.430 | 0.102 |
| S12 | 3.430 | | | | 3.430 | 0.055 |
| S14 | 0.144 | 21.617 | | | 21.761 | 0.357 |
| S16 | 7.577 | 21.657 | 8.000 | | 37.234 | 0.517 |
| S18 | 6.860 | 0.597 | | | 7.457 | 0.117 |
| S20 | 0.717 | 21.060 | 8.000 | | 29.777 | 0.406 |
| S22 | 0.573 | 0.040 | | | 0.613 | 0.010 |
| S24 | 0.144 | 4.210 | | | 4.354 | 0.072 |
| S26 | | 16.810 | 8.000 | | 28.810 | 0.325 |
| S28 | | | | 42.000 | 42.000 | 0.072 |
| S30 | | 16.810 | 8.000 | 42.000 | 66.810 | 1.063 |
| S32 | 3.430 | | | | 3.430 | 0.055 |
| S34 | 40.000 | | | | 40.000 | 0.610 |
| S36 | 40.000 | 16.810 | | 42.000 | 98.810 | 1.558 |
| S38 | 3.430 | | 8.000 | | 11.430 | 0.097 |
| S40 | | 16.810 | | 42.000 | 58.810 | 1.007 |
| S42 | | 16.810 | | | 16.810 | 0.274 |
| S44 | | 0.597 | | | 0.597 | 0.010 |

The present invention is further described in the following non-limiting examples.

EXAMPLE 1

CL-20 was crystallized to the epsilon polymorph by combining about 16 pounds (dry basis) of water wet CL-20, 9 gallons of ethyl acetate and about 3 gallons of water in an agitated vessel. The mixture was stirred for ½ hour to dissolve the CL-20, then agitation was stopped and the mixture settled for ½ hour. Two liquid phases separated. The upper aqueous phase was discarded. The lower organic phase was drained through a bottom valve to a clean, dry agitated vessel. About 5 pounds of anhydrous magnesium sulfate were added to the organic phase and the mixture was agitated for one hour to dry the solution. Agitation was stopped and the mixture settled for ½ hour; the magnesium sulfate settled to the bottom of the vessel leaving a clean solution above which was pumped through a filter to a clean dry agitated vessel. About 1.3 pounds of epsilon CL-20 were combined with the dried solution; all this seeding was done at one time. About 20 gallons of heptane were added to the seeded solution evenly over a two hour period. The resulting slurry was drained through a bottom valve into 15 gallons of water. The spent heptane/ethyl acetate liquor floated to the top of water and was decanted. The CL-20 sank to the bottom of the water. After most of the spent organic liquor had been decanted, the CL-20 was agitated in the water to remove more of the organic liquor adhering to the crystals. Then most of the water was decanted from the CL-20. About 12.5 pounds of epsilon CL-20 was recovered. The following Tables 2 and 3 summarizes data comparing polycrystalline Σ-CL-20, Σ-CL-20 (present invention), and HMX.

TABLE 2

| | Cl-20 Sensitivity | | |
| --- | --- | --- | --- |
| | ε-cl-20 (polycrystalline) | ε-CL-20 (rounded, XH-1) | HMX (20 micron) |
| Impact (in., 50%) | 19.40 | 36.6 | 26.80 |
| ABL Impact (cm, t.i.l.) | 1.1–1.8 | 3.5 | 1.8 |
| ABL Friction (Ibs/@ft/sec) | 100 @ 4 | 100 @ 4 | 50–100 @ 4 |
| ESD (J, 50%) | 0.68 | 0.50 | 0.57 |

TABLE 3

| Bulk Density measurements | | | |
| --- | --- | --- | --- |
| | Bulk Density (measured, g/ml) | Density (X-ray, g/ml) | % theoretical density |
| RDX | 1.794–1.797 | 1.82 | 98.6–98.7 |
| β-HMX | 1.894–1.901 | 1.96 | 96.6–97.0 |
| ε-CL-20 (XH-1) | 2.036 | 2.044 | 99.6 |
| PCL-55 | 2.032 (by distribution) | 2.044 | 99.4 |
| PCL-57 | 2.028 (by picnometer) | 2.044 | 99.2 |
| PCLX-74 | 2.022 (by picnometer) | 2.044 | 98.9 |

The distribution means used the method described by Borne. Microstructure effect on the shock sensitivity of cost plastic bonded explosives, $6^e$ Congres International de Pyrotechnic du "Groupe de Travail de Pyrotechnie," Europyro 95, pages 125–131, Tours, France (Jun. 5–9, 1995), the complete disclosure of which is incorporated by reference. The picnometer is a more direct method that only gives a 50% number. Lots XH-1, PCL-55 and PCL-57 were done with ethyl acetate/heptane. PCLX-74 was done with ethyl acetate/chloroform.

An increase in 1 to 3% in theroretical density means higher performance, and utility for applications requiring such higher performance which otherwise would not be possible using the conventional CL-20 product. The higher crystal quality of the present Σ-CL-20 crystals signifies a low void content, which, in principle, means as low as possible theoretical sensitivity for this material.

EXAMPLE 2

CL-20 was crystallized to the epsilon polymorph (ε-CL-20) as follows: To 3.85 kg of crude, moist CL-20 were added 7.6 L of ethyl acetate and 1 L of water. The mixture was stirred until all CL-20 dissolved. The layers were separated and the aqueous layer discarded. The organic layer was dried with anhydrous magnesium sulfate (roughly 200 g) then anhydrous potassium carbonate (roughly 100 g) was added to scavenge any acidic species. The inorganic salts were removed by filtration and the organics transferred to a stirred reactor. To the slowly stirred ethyl acetate solution were added 19 L of toluene over 2.5 hours. Near the beginning of the toluene addition, 1 to 200 g of seed epsilon crystals were added. After completion of the toluene addition, the resulting ε-CL-20 was collected by filtration. The residual organic solvents were largely removed by air drying and the resulting ε-CL-20 was wetted with water.

EXAMPLE 3

CL-20 was crystallized to the epsilon polymorph (ε-CL-20) according to the procedure of Example 2, except that heptane was used instead of toluene.

EXAMPLE 4

CL-20 was crystallized to the epsilon polymorph (ε-CL-20) according to the procedure of Example 2, except that carbonate was added to the aqueous layer instead of the dried organic layer.

EXAMPLE 5

CL-20 was crystallized to the epsilon polymorph (ε-CL-20) according to the procedure of Example 2, except that magnesium sulfate was not used to dry the organic layer. Instead, the aqueous layer was made basic, the layers were separated, 1 additional liter of ethyl acetate was added, and the ethyl acetate/water azeotrope was removed under vacuum (45° C.–50° C.) until no water layer was visible. Then another 200 ml of liquid was evaporated to be sure all water was removed. Crystallization proceeded with toluene as in Example 2.

EXAMPLE 5

CL-20 is crystallized to the epsilon polymorph ($\epsilon$-CL-20) according to the procedure of Example 2, except that heptane was used instead of toluene.

EXAMPLE 6

Figure 2:
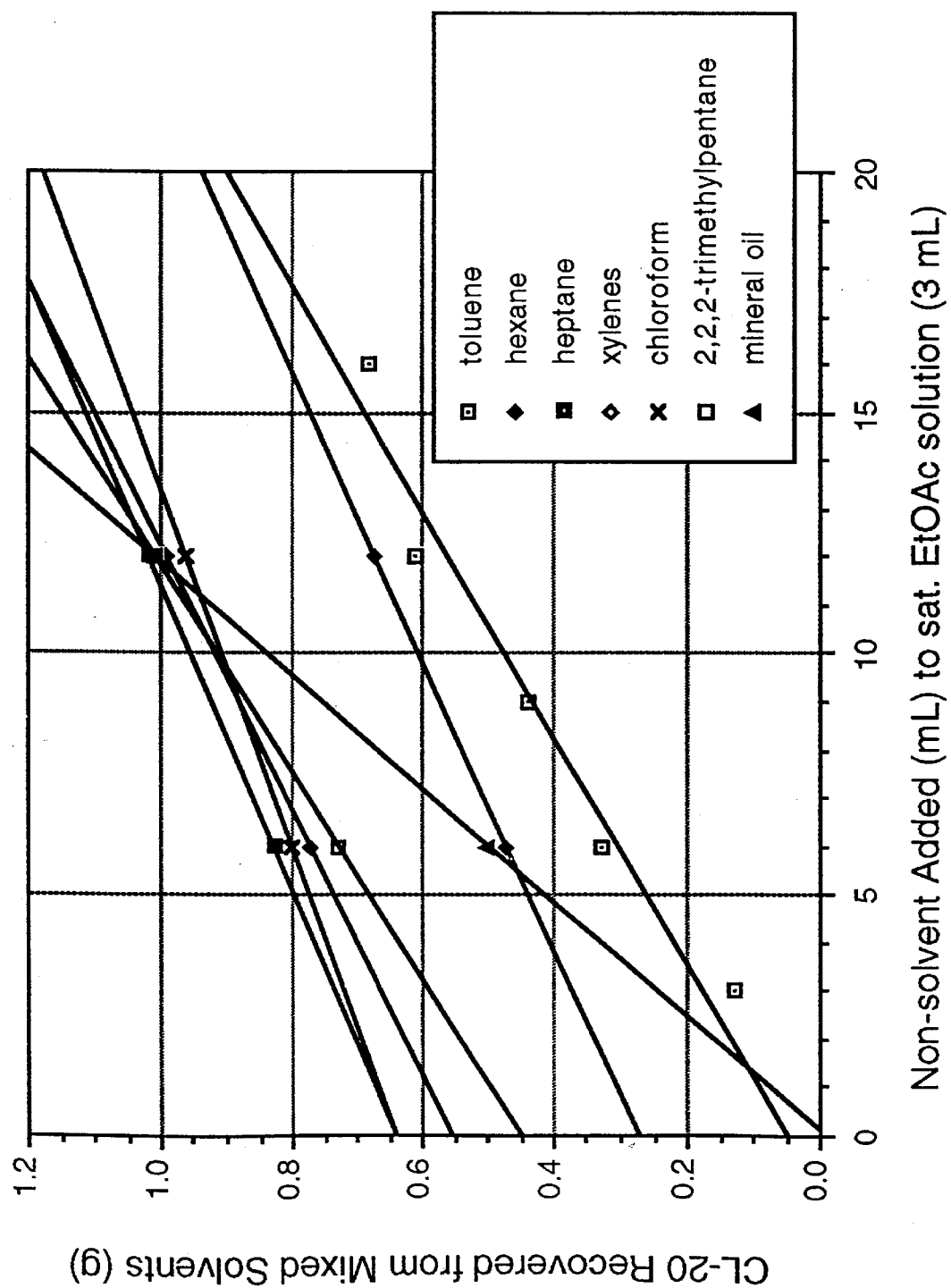
FIG. 2 is a graph reporting the amount of CL-20 recovered from mixed solvents as a function of the amount of non-solvent added to a saturated ethyl acetate solution of CL-20.

A nearly saturated solution of CL-20 in ethyl acetate (roughly 0.4 g of CL-20 per ml of EtOAc) was prepared. To 3 ml of this solution was added a measured amount of a second, CL-20 non-solvent in the quantity noted in FIG. 2. The resulting slurry of CL-20 was allowed to stir for roughly 0.5 hours and then filtered. The CL-20 was dried and weighed. The amount recovered was reported in FIG. 2. It should be noted that there will be some loss of CL-20 in this process. This error should be of a similar magnitude for all the solvent systems tested. Therefore, the data reported in FIG. 2 should not be used to quantitatively predict the amount of material to be recovered in a larger scale crystallization. At a larger scale, the percentage loss will be reduced. Because of this, the data reported in FIG. 2 should be used to judge relative merit of each non-solvent.

From the foregoing, it will be appreciated that the present invention provides a process and system of crystallizing CL-20 which does not require or discharge chlorinated solvents. The present invention also permits efficient recycling of the solvent within the crystallization process. Importantly, the present invention provides a process of crystallizing CL-20 which produces predominantly $\epsilon$-polymorph CL-20.

The present invention may be embodied in other specific forms without departing from its essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A process of crystallizing $\epsilon$-polymorph CL-20 (2,4,6, 8,10,12-hexanitro-2,4,6,8,10,12-hexaazatetracyclo[5.5.0.0$^{5,}$ $^{9}$0$^{3,11}$]-dodecane) comprising the steps of:
    (a) drying a wet CL-20 solvent solution containing a quantity of CL-20 dissolved therein, thereby forming a dry solvent solution containing the CL-20, wherein solubility of CL-20 in the solvent is greater than 20% weight/volume (g/ml);
    (b) adding a low density, CL-20 non-solvent to the dry solvent solution to cause precipitation of $\epsilon$-polymorph CL-20 crystals, wherein the solubility of CL-20 in the non-solvent is less than 1% weight/volume (g/ml); and
    (c) separating the precipitated $\epsilon$-polymorph CL-20 crystals from the non-solvent and the solvent by adding a sufficient quantity of a polar dense solvent to displace the non-solvent and the solvent from the surface of the $\epsilon$-polymorph CL-20 crystals.

2. A process of crystallizing $\epsilon$-polymorph CL-20 as defined in claim 1, wherein said drying step is accomplished by removal of a solvent/water azeotrope.

3. A process of crystallizing $\epsilon$-polymorph CL-20 as defined in claim 1, wherein the CL-20 solvent is selected from ethyl acetate, methyl acetate, isopropyl acetate, butyl acetate, THF, and MEK.

4. A process of crystallizing $\epsilon$-polymorph CL-20 as defined in claim 1, wherein the CL-20 solvent is ethyl acetate.

5. A process of crystallizing $\epsilon$-polymorph CL-20 as defined in claim 1, wherein the CL-20 non-solvent does not contain chlorine.

6. A process of crystallizing $\epsilon$-polymorph CL-20 as defined in claim 5, wherein the CL-20 non-solvent is selected from hexane, cyclohexane, heptane, octane, benzene, toluene, xylene, mineral oil, petroleum ethers, and ligroin.

7. A process of crystallizing $\epsilon$-polymorph CL-20 as defined in claim 1, wherein the dense solvent is water.

8. A process of crystallizing $\epsilon$-polymorph CL-20 as defined in claim 1, wherein the dry CL-20 solvent solution contains less than 1.5%, by weight of water.

9. A process of crystallizing $\epsilon$-polymorph CL-20 as defined in claim 1, further comprising the step of adding a base to the CL-20 solvent solution containing a quantity of CL-20 dissolved therein to neutralize acidic species.

10. A process of crystallizing $\epsilon$-polymorph CL-20 as defined in claim 9, wherein the base is selected from $Na_2CO_3$, $K_2CO_3$, $NaHCO_3$, $KHCO_3$, NaOH, and KOH.

11. A process of crystallizing $\epsilon$-polymorph CL-20 (2,4,6, 8,10,12-hexanitro-2,4,6,8,10,12-hexaazatetracyclo[5.5.0.0$^{5,}$ $^{9}$0$^{3,11}$]-dodecane) comprising the steps of:
    (a) dissolving a quantity of CL-20 in a solution containing a CL-20 solvent and water to form an aqueous phase and a wet CL-20 solvent phase, wherein the CL-20 is dissolved in the wet CL-20 solvent phase, and wherein solubility of CL-20 in the solvent is greater than 20% weight/volume (g/ml);
    (b) drying the wet CL-20 solvent phase thereby forming a dry CL-20 solvent phase containing the CL-20;
    (c) adding a base to the CL-20 solvent phase to neutralize acidic species;
    (d) adding a low density, CL-20 non-solvent to the dry CL-20 solvent phase to cause crystallization of $\epsilon$-polymorph CL-20 crystals, wherein the solubility of CL-20 in the non-solvent is less than 1% weight/volume (g/ml);
    (e) separating the $\epsilon$-polymorph CL-20 from the non-solvent and the CL-20 solvent by adding sufficient water to displace the non-solvent and the solvent from the surface of the $\epsilon$-polymorph CL-20 crystals such that the $\epsilon$-polymorph CL-20 is wet; and
    (f) collecting the wet $\epsilon$-polymorph CL-20.

12. A process of crystallizing $\epsilon$-polymorph CL-20 as defined in claim 11, wherein said drying step is accomplished by removal of a solvent/water azeotrope.

13. A process of crystallizing $\epsilon$-polymorph CL-20 as defined in claim 11, wherein the CL-20 solvent is selected from ethyl acetate, methyl acetate, isopropyl acetate, butyl acetate, THF, and MEK.

14. A process of crystallizing $\epsilon$-polymorph CL-20 as defined in claim 11, wherein the CL-20 solvent is ethyl acetate.

15. A process of crystallizing $\epsilon$-polymorph CL-20 as defined in claim 11, wherein the CL-20 non-solvent does not contain chlorine.

16. A process of crystallizing $\epsilon$-polymorph CL-20 as defined in claim 11, wherein the CL-20 non-solvent is selected from hexane, cyclohexane, heptane, octane, benzene, toluene, xylene, mineral oil, petroleum ethers, and ligroin.

17. A process of crystallizing $\epsilon$-polymorph CL-20 as defined in claim 11, further comprising the step of separating and recycling the non-solvent, the solvent, and excess water after formation of the wet CL-20.

18. A process of crystallizing $\epsilon$-polymorph CL-20 as defined in claim 11, wherein the dry CL-20 solvent phase contains less than 1.5%, by weight, water.

19. A process of crystallizing $\epsilon$-polymorph CL-20 as defined in claim 11, wherein the base is selected from $Na_2CO_3$, $K_2CO_3$, $NaHCO_3$, $KHCO_3$, $NaOH$, and $KOH$.

20. A process of crystallizing $\epsilon$-polymorph CL-20 as defined in claim 11, wherein $\epsilon$-polymorph CL-20 seed crystals are added to the solvent/non-solvent mixture to facilitate $\epsilon$-polymorph CL-20 crystallization.

21. A process of crystallizing $\epsilon$-polymorph CL-20 (2,4,6,8,10,12-hexanitro-2,4,6,8,10,12-hexaazatetracyclo[5.5.0.0$^{5,9}$0$^{3,11}$]-dodecane) comprising:

conveying a wet solution of a CL-20 solvent and CL-20 to a solution dryer, wherein solubility of CL-20 in the solvent is greater than 20% weight/volume (g/ml);

drying the wet solution of CL-20 solvent and CL-20 by removing a CL-20 solvent/water azeotropic mixture from the wet solution of CL-20 solvent and CL-20, thereby forming a dry solution of CL-20 solvent and CL-20;

adding a base to the solution of CL-20 solvent and CL-20 to neutralize acidic species;

conveying the dry solution of CL-20 solvent and CL-20 to a crystallizer vessel;

introducing a low density, CL-20 non-solvent to the crystallizer vessel, wherein the CL-20 non-solvent does not contain chlorine and wherein the solubility of CL-20 in the non-solvent is less than 1% weight/volume (g/ml);

introducing seed crystals of $\epsilon$-polymorph CL-20 to the crystallizer vessel to cause crystallization of $\epsilon$-polymorph CL-20 from the dry CL-20 solvent;

conveying crystallized $\epsilon$-polymorph CL-20, CL-20 solvent, and the CL-20 non-solvent to a CL-20 recovery tank;

introducing a sufficient quantity of water into the CL-20 recovery tank to displace the non-solvent and the CL-20 solvent from the surface of the $\epsilon$-polymorph CL-20 crystals such that the $\epsilon$-polymorph CL-20 is wet; and recovering the wet crystallized $\epsilon$-polymorph CL-20.

22. A process of crystallizing $\epsilon$-polymorph CL-20 as defined in claim 21, further comprising the steps of:

dissolving CL-20 in the CL-20 solvent in a dissolver vessel; and conveying a waste water phase and a wet solution of CL-20 solvent and CL-20 from the dissolver vessel to a first decanter, wherein the first decanter removes the waste water phase from the wet solution of CL-20 solvent and CL-20.

23. A process of crystallizing $\epsilon$-polymorph CL-20 as defined in claim 22, further comprising separating and recycling the non-solvent, the solvent, and excess water after formation of the wet crystallized $\epsilon$-polymorph CL-20.

24. A process of crystallizing $\epsilon$-polymorph CL-20 as defined in claim 23, wherein the CL-20 solvent is selected from ethyl acetate, methyl acetate, isopropyl acetate, butyl acetate, THF, and MEK.

25. A process of crystallizing $\epsilon$-polymorph CL-20 as defined in claim 23, wherein the CL-20 solvent is ethyl acetate.

26. A process of crystallizing $\epsilon$-polymorph CL-20 as defined in claim 24, wherein the CL-20 non-solvent is selected from hexane, cyclohexane, heptane, octane, benzene, toluene, xylene, petroleum ethers, and ligroin.

27. A process of crystallizing $\epsilon$-polymorph CL-20 as defined in claim 24, wherein the base is selected from $Na_2CO_3$, $K_2CO_3$, $NaHCO_3$, $KHCO_3$, $NaOH$, and $KOH$.

* * * * *